United States Patent
Mendrok-Edinger

(10) Patent No.: US 12,220,477 B2
(45) Date of Patent: *Feb. 11, 2025

(54) COSMETIC COMPOSITION COMPRISING SPECIFIC HYPERBRANCHED COPOLYMERS AND ORGANIC UV FILTERS

(71) Applicant: DSM IP ASSETS B.V., Heerlen (NL)

(72) Inventor: Christine Mendrok-Edinger, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 876 days.

This patent is subject to a terminal disclaimer.

(21) Appl. No.: 17/296,486

(22) PCT Filed: Nov. 26, 2019

(86) PCT No.: PCT/EP2019/082490
§ 371 (c)(1),
(2) Date: May 24, 2021

(87) PCT Pub. No.: WO2020/109263
PCT Pub. Date: Jun. 4, 2020

(65) Prior Publication Data
US 2022/0023190 A1    Jan. 27, 2022

(30) Foreign Application Priority Data

Nov. 26, 2018  (EP) .................... 18208232

(51) Int. Cl.
*A61K 8/88* (2006.01)
*A61Q 17/04* (2006.01)

(52) U.S. Cl.
CPC ............ *A61K 8/88* (2013.01); *A61Q 17/04* (2013.01); *A61K 2800/30* (2013.01); *A61K 2800/522* (2013.01); *A61K 2800/544* (2013.01); *A61K 2800/591* (2013.01)

(58) Field of Classification Search
None
See application file for complete search history.

(56) References Cited

U.S. PATENT DOCUMENTS 5,192,534 A * 3/1993 Grollier .................. A61K 8/37
424/59

FOREIGN PATENT DOCUMENTS

| | | |
|---|---|---|
| CN | 101505712 | 8/2009 |
| CN | 103347491 | 10/2013 |
| CN | 104619309 | 5/2015 |
| CN | 104640931 | 5/2015 |
| EP | 2883533 | 6/2015 |
| EP | 2 794 729 | 4/2016 |
| GB | 2552922 | 2/2018 |
| JP | 2011-524883 | 9/2011 |
| JP | 2015-529674 | 10/2015 |
| JP | 2015-529737 | 10/2015 |
| WO | 2006/013200 | 2/2006 |
| WO | 2007/144189 | 12/2007 |
| WO | 2009/153334 | 12/2009 |
| WO | 2014/040811 | 3/2014 |
| WO | 2014/041019 | 3/2014 |
| WO | 2017/174214 | 10/2017 |

OTHER PUBLICATIONS

International Search Report for PCT/EP2019/082490 dated Jan. 10, 2020, 5 pages.
Written Opinion of the ISA for PCT/EP2019/082490 dated Jan. 10, 2020, 6 pages.
Research Disclosures, "Research Disclosure", Oct. 1, 2014, vol. 606, No. 33, 6 pages.
Notice of Registration and Notice of Granting of a Patent Right for an Invention with Search Report, CN Application No. 201980076840.7, Jun. 27, 2024.

* cited by examiner

*Primary Examiner* — Nannette Holloman
(74) *Attorney, Agent, or Firm* — NIXON & VANDERHYE P.C.

(57) ABSTRACT

The present invention relates to cosmetic compositions which comprise a hyperbranched copolymer of the monomers dodecenyl succinic acid anhydride, diisopropanol amine and bis-dimethylaminopropyl amine having quaternary terminal groups and a liquid and/or solid organic UV-filter. The copolymer is used in a cosmetic composition comprising the UV-filter for reducing the material transfer to a contacted surface. Preferably the copolymer is polyquatemium-110.

19 Claims, No Drawings

COSMETIC COMPOSITION COMPRISING SPECIFIC HYPERBRANCHED COPOLYMERS AND ORGANIC UV FILTERS

CROSS-REFERENCE TO RELATED APPLICATIONS

This application is the U.S. national phase of International Application No. PCT/EP2019/082490 filed Nov. 26, 2019 which designated the U.S. and claims priority to EP 18208232.1 filed Nov. 26, 2018, the entire contents of each of which are hereby incorporated by reference.

TECHNICAL FIELD

The present invention relates to the field of cosmetics, particularly to field of sun care.

BACKGROUND OF THE INVENTION

In the field of cosmetic the details of a cosmetic composition, i.e. a formulation, are very sensitive to aspects of texture, feel and visual aspects.

A big problem is that material of such a composition when applied to a surface, particularly to the skin, can be transferred to another surface when said other surface is brought in contact with said composition. Such a transfer is negative in two ways: First of all, the transfer of the material is not desired as it is removed from the site of action, such as treating, moisturizing or protecting the skin. Secondly, the surface of contact is contaminated with said material. Particularly fabrics, such as clothes can be stained. Furthermore, decorative or functional surfaces can be contaminated which is negative for the functionality, respectively, for their visual or aesthetic properties. Particularly, displays of mobile phones, screens, or touch screens can be negatively affected by such material transfer.

SUMMARY OF THE INVENTION

Hence, there exist a great desire to reduce such a transfer of cosmetic compositions from surface to surface when the surfaces are contacted.

Surprisingly, it has been found that the cosmetic compositions of claim 1 can solve this problem.

It has been found that the combination of a specific hyperbranched copolymer and organic UV filter(s) heavily reduces the material transfer of such compositions to contacted surfaces.

Further aspects of the invention are subject of further independent claims. Particularly preferred embodiments are subject of dependent claims.

DETAILED DESCRIPTION OF THE INVENTION

In a first aspect the present invention relates to a cosmetic composition comprising
a hyperbranched copolymer of the monomers
  (i) dodecenyl succinic acid anhydride
  (ii) diisopropanol amine
  (iii) bis-dimethylaminopropyl amine
having terminal groups of formula

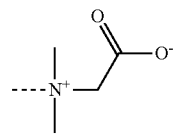

and having a molecular weight Mn of between 1200 and 4000 g/mol;
and at least one liquid organic UV filter and/or at least one solid organic UV filter.

The term "molecular weight Mn" stands for the number average molecular weight.

The term "UV filter" in the present document stands for a substance that absorbs ultraviolet light (=UV light), i.e. electromagnetic radiation of the wavelength between 280 and 400 nm. UV(A) filters are UV filters that absorb UV(A) light, i.e. electromagnetic radiation of the wavelength between 315 and 400 nm.

UV(B) filters are UV filters that absorb UV(B) light, i.e. electromagnetic radiation of the wavelength between 280 and 315 nm.

A liquid organic UV filter is liquid at ambient temperature (i.e. 25° C.).

A solid organic UV filter is solid at ambient temperature (i.e. 25° C.).

The term "preparation" or "formulation" is used in this document as equivalent to the term "composition".

The term "material transfer" in this document means the mass transfer of the cosmetic composition or some ingredients thereof when the cosmetic composition is applied to a surface and afterwards said surface is brought in contact with a surface of a different object and separated again. By this contact some material is transferred from the first surface to the surface of the different object. The amount of material transferred can be determined by measuring the weight gain of the second object.

The hyperbranched copolymer is preferably prepared by the following consecutive steps of:
  a1) polymerizing the monomers (i) and monomers (ii) and monomers (iii) to yield a polyesteramide having terminal dimethyl amino groups of the formula

a2) quaternization of the dimethyl amino groups of the polyesteramide of step a1) by 2-chloroacetate, particularly by sodium 2-chloroacetate.

Details for the polymerization step a1) to yield the respective polyesteramide having terminal dimethyl amino groups of the formula

are disclosed for example by EP 2 794 729 B1.

Preferably in the polymerization step a1) the monomer (iii) is added to a mixture of monomers (ii) and (iii) under stirring, followed by heating.

Details of the quaternization step a2) are disclosed as well by EP 2 794 729 B1. Therefore, the entire content of EP 2 794 729 B1 is hereby incorporated by reference.

The amount of the hyperbranched copolymer of the monomers
(i) dodecenyl succinic acid anhydride
(ii) diisopropanol amine
(iii) bis-dimethylaminopropyl amine
having terminal groups of formula

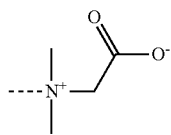

and having a molecular weight Mn of between 1200 and 4000 g/mol
in the cosmetic composition is typically between 0.1 and 3% by weight, based on the total weight of the cosmetic composition.

It is preferred that the molar ratio of the monomers (i) to monomers (ii) is between 5:1 and 0.5:1, particularly between 4:1 and 1:1, preferably between 3:1 and 3:2.

It is further preferred that the molar ratio of the monomers (i) to monomers (iii) is between 5:1 and 0.5:1, particularly between 3:1 and 1:1, preferably between 2.5:1 and 1.1:1.

The hyperbranched copolymer has preferably a number average molecular weight $M_n$ of between 1400 and 3000 g/mol, preferably between 2100 and 2300 g/mol.

Preferably, the hyperbranched polymer is polyquaternium-110, also identified by CAS Number 1323977-82-7.

The cosmetic composition further comprises at least one liquid organic UV filter and/or at least one solid organic UV filter.

Suitable liquid organic UV-filter absorb light in the UVB and/or UVA range and are liquid at ambient temperature (i.e. 25° C.). Such liquid UV-filter are well known to a person in the art and encompass in particular cinnamates such as e.g. octyl methoxycinnamate (PARSOL® MCX) and isoamyl methoxycinnamate (Neo Heliopan® E 1000), salicylates such as e.g. homosalate (3,3,5 trimethylcyclohexyl 2-hydroxybenzoate, PARSOL® HMS) and ethylhexyl salicylate (also known as ethylhexyl salicylate, 2 ethylhexyl 2-hydroxybenzoate, PARSOL® EHS), acrylates such as e.g. octocrylene (2 ethylhexyl 2-cyano-3,3-diphenylacrylate, PARSOL® 340) and ethyl 2-cyano-3,3 diphenylacrylate, esters of benzalmalonic acid such as in particular dialkyl benzalmalonates such as e.g. di(2-ethylhexyl) 4-methoxybenzalmalonate and polysilicone 15 (PARSOL® SLX), dialkylester of naphthalates such as e.g. diethylhexyl 2,6-naphthalate (Corapan® TQ), syringylidene malonates such as e.g. diethylhexyl syringylidene malonate (Oxynex® ST liquid) as well as benzotriazolyl dodecyl p-cresol (Tinoguard® TL) as well as benzophenone-3 and drometrizole trisiloxane.

It has been observed that polysilicone based organic UV filters (such as polysilicon 15) have a less pronounced reduction in material transfer. Hence, it is preferred that the Cosmetic composition does not comprise a polysilicon based organic UV filter.

Particular advantageous liquid organic UV-filter are octyl methoxycinnamate, homosalate, ethylhexyl salicylate, octocrylene, diethylhexyl 2,6-naphthalate, diethylhexyl syringylidene malonate, benzotriazolyl dodecyl p-cresol, benzophenone-3, drometrizole trisiloxane as well as mixtures thereof.

In a preferred embodiment, the liquid UV filter is a liquid UV(B) filter which is selected from the group consisting of ethylhexyl methoxycinnamate, octocrylene, homosalate, ethylhexyl salicylate, benzophenone-3 and drometrizole trisiloxane.

Suitable solid organic UV-filter absorb light in the UVB and/or UVA range and are solid at ambient temperature (i.e. 25° C.). Particularly suited solid UV-filters are of the group consisting of bis-ethylhexyloxyphenol methoxyphenyl triazine, butyl methoxydibenzoyl methane, methylene bis-benzotriazolyl tetramethylbutylphenol, diethylamino hydroxybenzoyl hexyl benzoate, ethylhexyl triazone, diethylhexyl butamido triazone, 4-methylbenzylidene camphor and 1,4-di(benzoxazol-2'-yl)benzene.

A preferred solid organic UV(A) filter is a UV(A) filter which is selected from the group consisting of bis-ethylhexyloxyphenol methoxyphenyl triazine, butyl methoxydibenzoyl methane, methylene bis-benzotriazolyl tetramethylbutylphenol and diethylamino hydroxybenzoyl hexyl benzoate.

A preferred solid organic UV(B) filter is a UV(B) filter which is selected from the group consisting of ethylhexyl triazone (=Uvinul T150), diethylhexyl butamido triazone (=Uvasorb HEB), and 4-methylbenzylidene camphor (=Parsol 5000).

The total amount of organic UV filter(s) depends strongly on the targeted UV protection.

It is preferred that the amount of a solid organic UV filter, particular of solid organic UV(A) filter, is selected in the range of 0.1 to about 6 wt.-%, preferable in the range of 0.5 to 5 wt.-%, most preferably in the range of 1 to 4 wt.-%.

It is further preferred that amount of a solid organic UV filter, particular of solid organic UV(B) filter, is selected in the range of 0.1 to about 6 wt.-%, preferable in the range of 0.5 to 5 wt.-%, most preferably in the range of 1 to 4 wt.-%.

It is even further preferred that amount of a liquid organic UV filter, particular of liquid organic UV(B) filter, is selected in the range of 0.1 to about 10 wt.-%, preferable in the range of 0.5 to 8 wt.-%, most preferably in the range of 1 to 6 wt.-%.

In one of the embodiment the cosmetic composition comprises at least two UV filters of which at least one is a solid or liquid organic UV(A) filter and of which at least one is a solid or liquid organic UV(B) filter.

In said embodiment it is preferred that the composition comprises at least two organic UV filters of which at least one is a solid or liquid organic UV(A) filter and of which at least one is a solid or liquid organic UV(B) filter.

Preferred is a combination of at least one solid organic UV(A) filter and at least one liquid organic UV(B) filter.

Particularly preferred in said embodiment is a combination of
at least one solid organic UV(A) filter which is selected from the group consisting of bis-ethylhexyloxyphenol methoxyphenyl triazine, butyl methoxydibenzoyl methane, methylene bis-benzotriazolyl tetramethylbutylphenol and diethylamino hydroxybenzoyl hexyl benzoate and
at least one liquid organic UV(B) filter selected, from the group consisting of ethylhexyl methoxycinnamate, octocrylene, homosalate, ethylhexyl salicylate and benzophenone-3, drometrizole trisiloxane The total amount of organic UV filter (s) depends strongly on the targeted UV protection of said composition and is typically in the range of between 1 to 50% by weight, preferably between 5 to 40% by weight, based on the total weight of said composition.

A sun creme with an SPF 15, for example, comprises preferably a total amount of organic UV filter (s) of between 4 to 20% by weight, more preferably between 7 and 15% by weight, based on the total weight of said composition.

A sun creme with an SPF 30, for example, comprises preferably a total amount of organic UV filter (s) of between 10 to 40% by weight, more preferably between 15 and 25% by weight, based on the total weight of said composition.

A sun creme with an SPF 50, for example, comprises preferably a total amount of organic UV filter (s) of between 15 to 50% by weight, more preferably between 20 and 40% by weight, based on the total weight of said composition.

The cosmetic composition typically comprises other ingredients which are suitable for the use in cosmetic compositions.

The cosmetic composition further preferably comprises at least one oil.

The term "oil" in the present description stands for a water-insoluble, organic, natural, or synthetic, cosmetically suitable oil which preferably has a liquid or viscous consistency at 23° C. "Water-insoluble" in this context refers to a water-solubility of the oil of not more than 2% by weight at 20° C.

It is preferred that the oil is an oil with a polarity index of between 5 and 55 mN/m, preferably either in the range of 55-24 mN/m or in the range of 18-5 mN/m, more preferably either in the range of 50 and 30 mN/m in the range of 15 and 5 mN/m.

The term "polarity index" is a parameter which is known to the person skilled in the art. The polarity of an oil is defined as the polarity index (interfacial tension) of the oil with respect to water. The interfacial tension, i. e. the polarity index, can be particularly determined using a ring tensiometer (e.g., Krüss K 10), which measures the interfacial tension in mN/m in analogy to the ASTM method D971-99a (2004).

The oils are particularly oils of the chemical groups alkanes, triglycerides, ester oils or glycol esters.

The oil is preferably selected from the group consisting of dibutyl adipate, castor oil, calendula oil, wheatgerm oil, di-C12-13 alkyl tartrate, propylene glycol monoisostearate and cocoglycerides, particularly from the group consisting of di-C12-13 alkyl tartrate, dibutyl adipate and cocoglycerides.

Preferred oils with a polarity index of between 50 and 30 mN/m is an oil selected from the group consisting of isoparaffin (C12-C14), cycloparaffin, polydecene, squalane, hydrogenated polyisobutene, isohexadecane, paraffin oil perliquidum, polydimethylsiloxane, isoeicosane, ethoxydiglycol oleate, decyl olivate, dioctylcyclohexane, paraffin oil subliquidum, paraffinum liquidum, isocetyl palmitate, cyclopentasiloxane, dicaprylyl carbonate, octyl isostearate, trimethylhexyl isononanoate, 2-ethylhexyl isononanoate, dicaprylyl ether, dihexyl carbonate and octyl cocoate, particularly from the group consisting of di-caprylyl carbonate, paraffinum liquidum, and squalane.

Preferred oils with a polarity index the range 18-5 mN/m are di-C12-13 alkyl tartrate, dibutyl adipate or cocoglycerides, even more preferred di-C12-13 alkyl tartrate or dibutyl adipate.

The total amount of the oil(s), particularly of oil(s) with a polarity index of either in the range of 55-24 mN/m or in the range of 18-5 mN/m is preferably in the range between 2-20% by weight, particularly 3-15% by weight, based on the total weight of the cosmetic composition.

The cosmetic composition further preferably comprises at least one emulsifier, preferably an anionic emulsifier. Preferably the anionic emulsifier is an anionic emulsifier selected from the group consisting of potassium cetyl phosphate, disodium cetearyl sulfosuccinate, sodium stearoyl glutamate, sodium stearoyl lactylate, glyceryl stearate citrate and sodium cocoyl isethionate.

Potassium cetyl phosphate is commercially available as Amphisol® K at DSM Nutritional Products Ltd Kaiseraugst.

The amount of emulsifier is preferably in the range between 0.1-6.0% by weight, more preferably between 0.25-5.0% by weight, particularly between 0.5-4.0% by weight, based on the total weight of the cosmetic composition.

The composition is preferably sulfate-free.

Hence, the cosmetic composition is preferably particularly free of sulfates of the group consisting of alkyl sulfates, alkyl ether sulfates, alkyl amido ether sulfates, alkylaryl polyether sulfates and monoglycerides sulfate as well as mixtures thereof.

The term "free" as used in the present document, for example in "sulfate-free", is used to mean that the respective substance is only present at amounts of less than 0.5% by weight, particularly less than 0.1% by weight, more particularly below 0.05% by weight, relative to the weight of the composition. Preferably, "free" means that the respective substance is completely absent in the composition.

The term "sulfate-free" is used in the present document to mean that the composition is free of any anionic tenside having a terminal anionic group of the formula

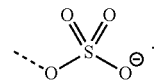

The cosmetic composition is preferably free of cationic emulsifiers. Typical example for such cationic emulsifiers are isostearamidopropyl dimethylamine, stearalkonium chloride, stearamidoethyl diethylamine, behentrimonium methosulfate, behenoyl PG-trimonium chloride, cetrimonium bromide, behenamidopropyl dimethylamine behenate, brassicamidopropyl dimethylamine, stearamidopropyl dimethylamine stearate, cocamidopropyl PG-dimonium chloride, distearoylethyl hydroxyethylmonium methosulfate, dicocoylethyl hydroxyethylmonium methosulfate, distearoylethyl dimonium chloride, shea butter amidopropyltrimonium chloride, behenamidopropyl dimethylamine, brassicyl isoleucinate esylate, acrylamidopropyltrimonium chloride/acrylates copolymer, linoleamidopropyl ethyldimonium ethosulfate, dimethyl lauramine isostearate, isostearamidopropyl laurylacetodimonium chloride, particularly behentrimonium chloride, distearyldimonium chloride, cetrimonium chloride, steartrimonium chloride, and palmitamidopropyltrimonium chloride.

The cosmetic composition further may comprise cosmetic carriers, excipients and diluents as well as additives and active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

Such possible ingredients of the cosmetic composition are particularly enhance the performance and/or consumer acceptability such as preservatives, antioxidants, fatty substances/oils, thickeners, softeners, light-screening agents, moisturizers, fragrances, co-surfactants, fillers, sequestering agents, cationic-, nonionic- or amphoteric polymers or mixtures thereof, acidifying or basifying agents, viscosity modifiers, and natural hair nutrients such as botanicals, fruit extracts, sugar derivatives and/or amino acids or any other ingredients usually formulated into cosmetic compositions. The necessary amounts of the adjuvants and additives can, based on the desired product, easily be chosen by a person skilled in the art in this field and will be illustrated in the examples, without being limited hereto.

In an advantageous embodiment, the compositions according to the present invention comprise from 50% to 99%, preferably from 60% to 98%, more preferably from 70% to 98%, such as in particular from 80% to 95% of a carrier, based on the total weight of the cosmetic composition.

The cosmetic composition comprises preferably water. In a particular advantageous embodiment, the carrier consists furthermore of at least 40 wt. %, more preferably of at least 50 wt.-%, most preferably of at least 55 wt.-% of water, such as in particular of 55 to 90 wt.-% of water.

Particularly suitable thickeners in all embodiments of the present invention are xanthan gum, gellan gum and/or carboxymethylcellulose. Most preferably in all embodiments of the present invention the thickener is xanthan gum or gellan gum.

Such thickener(s) are preferably used in an amount (total) selected in the range from 0.1 to 1 wt.-%, more preferably in an amount of 0.1 to 0.5 wt.-%, based on the total weight of the cosmetic composition.

It is preferred that the composition is free of polyvinylpyrrolidones (PVP), particularly free of alkylated polyvinylpyrrolidiones, such as copolymers of N-vinylpyrrolidones and hexadecane or eicosene, e.g. as commercially available as Antaron V-216 or Antaron V-220.

The cosmetic compositions according to the invention in general have a pH in the range from 3 to 10, preferably a pH in the range from 4 to 8 and most preferably a pH in the range from 4 to 7.5.. The pH can easily be adjusted as desired with suitable acids such as e.g. citric acid or bases such as NaOH according to standard methods in the art.

The cosmetic composition is preferably sulfate-free and/or free of parabens, and/or silicon oils and/or silicone surfactants and/or methylisothiazolidine and/or free of polyvinylpyrrolidones (PVP), particularly free of alkylated polyvinylpyrrolidiones.

The cosmetic composition is preferably a topical composition.

The term "topical" as used herein is understood here to mean external application to keratinous substances, which are in particular the skin, scalp, eyelashes, eyebrows, nails, mucous membranes and hair, preferably the skin.

As the topical compositions are intended for topical application, it is well understood that they comprise a physiologically acceptable medium, i.e. a medium compatible with keratinous substances, such as the skin, mucous membranes, and keratinous fibres. In particular, the physiologically acceptable medium is a cosmetically acceptable carrier.

The term "cosmetically acceptable carrier" refers to all carriers and/or excipients and/or diluents conventionally used in cosmetic compositions such as in particular in sun care products.

Preferably the cosmetic composition is a skin care preparation, decorative preparation, or a functional preparation.

Examples of skin care preparations are, in particular, light protective preparations, anti-ageing preparations, preparations for the treatment of photo-ageing, body oils, body lotions, body gels, treatment creams, skin protection ointments, skin powders, moisturizing gels, moisturizing sprays, face and/or body moisturizers, skin-tanning preparations (i.e. compositions for the artificial/sunless tanning and/or browning of human skin), for example self-tanning creams as well as skin lightening preparations.

Examples of functional preparations are cosmetic or pharmaceutical compositions containing active ingredients such as hormone preparations, vitamin preparations, vegetable extract preparations and/or anti-ageing preparations without being limited thereto.

The cosmetic composition is preferably a skin care composition.

In a most preferred embodiment, the cosmetic composition is a sun care composition. Sun care compositions are light-protective preparations (sun care products), such as sun protection milks, sun protection lotions, sun protection creams, sun protection oils, sun blocks or day care creams with a SPF (sun protection factor). Of particular interest are sun protection creams, sun protection lotions, sun protection milks and sun protection preparations.

The cosmetic compositions according to the present invention may be in the form of a suspension or dispersion in solvents or fatty substances, or alternatively in the form of an emulsion or micro emulsion (in particular of oil-in-water (O/W-) or water-in-oil (W/O-)type, silicone-in-water (Si/W-) or water-in-silicone (W/Si-)type, PIT-emulsion, multiple emulsion (e.g. oil-in-water-in oil (O/W/O-) or water-in-oil-in-water (W/O/W-)type), pickering emulsion, hydrogel, alcoholic gel, lipogel, one- or multiphase solution or vesicular dispersion or other usual forms, which can also be applied by pens, as masks or as sprays.

Preferred cosmetic compositions in all embodiments of the present invention are emulsions which contain an oily phase and an aqueous phase such as in particular O/W, W/O, Si/W, W/Si, O/W/O, W/O/W multiple or a pickering emulsions.

The total amount of the oily phase present in such emulsions is preferably at least 10 wt.-%, such as in the range from 10 to 60 wt.-%, preferably in the range from 15 to 50 wt.-%, most preferably in the range from 15 to 40 wt.-%, based on the total weight of the cosmetic composition.

The amount of the aqueous phase present in such emulsions is preferably at least 20 wt. %, such as in the range from 40 to 90 wt.-%, preferably in the range from 50 to 85 wt.-%, most preferably in the range from 60 to 85 wt.-%, based on the total weight of the cosmetic composition.

More preferably, the cosmetic compositions according to the present invention are in the form of an oil-in-water (O/W) emulsion comprising an oily phase dispersed in an aqueous phase in the presence of an O/W—respectively Si/W—emulsifier as such compositions show a significantly pronounced reduction of the transfer of the respective composition to surfaces. The preparation of such O/W emulsions is well known to a person skilled in the art.

The compositions in form of O/W emulsions according to the invention can be provided, for example, in all the formulation forms for O/W emulsions, for example in the form of serum, milk or cream, and they are prepared according to the usual methods. The compositions which are subject-matters of the invention are preferably intended for topical application and can in particular constitute a dermatological or cosmetic composition, for example intended for protecting human skin against the adverse effects of UV radiation (antiwrinkle, anti-ageing, moisturizing, anti-sun protection and the like).

It has been found that the cosmetic compositions have a strongly reduced material transfer to a contacted surface when the specific hyperbranched copolymer of the monomers
  (i) dodecenyl succinic acid anhydride
  (ii) diisopropanol amine
  (iii) bis-dimethylaminopropyl amine
  having terminal groups of formula

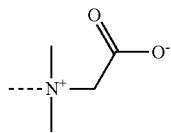

having a molecular weight Mn of between 1200 and 4000 g/mol is used together with at least one liquid organic UV filter and/or at least one solid organic UV filter in a cosmetic composition.

Hence, a further aspect of the present invention is the use of a hyperbranched copolymer of the monomers
  (i) dodecenyl succinic acid anhydride
  (ii) diisopropanol amine
  (iii) bis-dimethylaminopropyl amine
  having terminal groups of formula

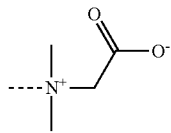

and having a molecular weight Mn of between 1200 and 4000 g/mol in a cosmetic composition comprising at least one liquid organic UV filter and/or at least one solid organic UV filter for reducing the material transfer to a contacted surface.

The amount of material transfer is determined by determination of the weight of the object (second object) before and after contact. Any weight gain after contact is due to a material transfer from the first to the second object. The reduction of material transfer is determined by comparing compositions according to the inventions with the respective (not according to the invention) composition which does not contain the above hyperbranched copolymer, respectively the UV filter. The reduction is expressed in % of the material transfer of the two measurements.

It has been found that the reduction of more than 30%, even more than 45%, particularly more than 55%, can be obtained.

The cosmetic composition is applied to a first surface. Said surface is preferably skin, particularly human skin. It has been found that using a porous sponge instead of skin is a good approach for simulate a material transfer from skin to another surface.

The surface of the contacted object (second object) is preferably a glass surface or a plastic or a surface of a fabric.

In case the surface is a fabric, this is very advantages to avoid an unwanted transfer of cosmetic composition to a fabric, particularly to clothes, as the cosmetic composition might stain the fabric.

Particularly, the contacted surface (i.e. surface of second object) is a glass surface.

Most preferably, the contacted surface (i.e. surface of second object) is an optical glass such as used for reading glasses or sunglasses or a display of screen of a smartphone display of a mobile phone, computer device or tablet.

By reducing the material transfer of the cosmetic composition, particularly the problem of marks, particularly finger marks, left on glasses such as optical glasses of instruments or visual glasses when said glass surface is contacted with fingers can be reduced or even avoided. Particularly, this can heavily reduce or even avoid any undesired effects on the light rays transmitted through said glass by said material left on the surface.

Furthermore, marks left on the surface of an aesthetic surface such as of a mirror or a highly glossy or highly mat surface such as a of a top coat of a car or furniture or piece of art, can be strongly reduced. This is very advantageous as such surfaces need a high amount of cleaning maintenance, if they are brought in contact with skin on which cosmetic compositions have been applied, particularly if they are touched by fingers which have been previously in contact with cosmetic compositions.

Marks left on the surface of display units, such as displays of mobile phones, screens, or touch screens of monitors, laptops, mobile phones or tablets can be strongly reduced. As a result of this, the readability can be improved. As the functionality of touch screens depends on surface aspects, the invention helps also to improve constant touch screen functionality without excessive need of cleaning said glass surface.

The reduction of material transfer also heavily reduces the labour and cost involved in the cleaning of said surfaces when they are contacted with skin.

EXAMPLES

The present invention is further illustrated by the following experiments. These examples are illustrative only and are not intended to limit the scope of the invention in any way.

Preparation of Hyperbranched Copolymer (HBC1)

The hyperbranched copolymer HBC1 of the monomers dodecenyl succinic acid anhydride and diisopropanol amine and bis-dimethylaminopropyl amine has been prepared according to example 3 in EP 2 794 729 B1 using 237.59 g of N,N-bis(N'N'-dimethylaminopropyl)amine and 112.6 g diisopropanol amine and 426.89 g of dodecenylsuccinic anhydride. After heating and vacuum, the residual carboxylic acid content of <0.3 meq/g (tritrimetrical analysis) AV=9.8 mg KOH/g and amine content of 2.99 meq/g (tritrimetrical analysis) and a molecular weight Mn=2240 was obtained. This product has been reacted with sodium chloroacetate in water and stirred at 80° C. until $^1$H-NMR analysis shows a complete conversion of the chloroacetate to obtain the hyperbranched copolymer HBC1 which has terminal groups of the formula

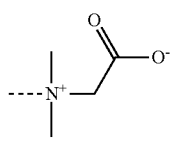

and a molecular weight Mn of 2.3 kDa.

The hyperbranched copolymer HBC1 was used as a 45% solution in water in the following experiments.

Material Transfer

The material transfer has been determined with the sponge test as outlined in the following:

- Cut a sponge cloth (Weitawip Claire, from Weita AG: cellulose/cotton fiber mixture, 200 g/m², 5 mm thickness) into pieces of 76 mm×26 mm
- Tare the sponge sample
- Apply 350 mg of the respective sample (=cosmetic composition) and distribute homogenously all over the sponge surface of 76 mm×26 mm
- Weigh the sponge with the applied sample
- Tare a microscope slide (glass plate 76 mm×26 mm×1 mm)
- Put the microscope slide (glass plate) on top of the sponge, on which a balance weight of 500 g (height: 6.3 cm, diameter at area of contact: 3.7 cm) is placed for 10 seconds to apply a specific pressure to the sample
- Remove cautiously vertically the microscope slide
- Weigh the removed microscope slide and determine accordingly the amount of sample transferred to the glass plate
- Repeat the test for each composition 10 times to receive an average value (mean value) for each sample.

Preparation of Cosmetic Compositions

The ingredients (in % by weight) of the oil phase according to table 1 have been combined and heated up to 85° C. The ingredients (in % by weight) of the water phase according to table 1 have been combined, stirred until the Xanthan Gum is completely dissolved and then heated up to 80° C. The two phases have been combined and homogenized for 1 minute with 10,000 rpm. Under moderate stirring the emulsion is cooled down to 35° C. In case a hyperbranched copolymer is used in an example, the respective hyperbranched polymer (in % by weight) is now added to the emulsion under stirring. The stirring has been continued until the emulsion reached room temperature. The amounts of ingredients of the compositions (sum up to 100% by weight) used are chosen so that each composition has a total weight of 70 grams.

TABLE 1

Material transfer of cosmetic compositions and respective reductions.

| Ingredient (INCI) | Ref. 1 | 1 | Ref. 2 | 2 | Ref. 3 | 3 | Ref. 4 | 4 |
|---|---|---|---|---|---|---|---|---|
| Oil Phase | | | | | | | | |
| potassium cetyl phosphate | 2.0 | 2.0 | 2.0 | 2.0 | 2.0 | 2.0 | 2.0 | 2.0 |
| dibutyl adipate | 5.0 | 5.0 | 5.0 | 5.0 | 5.0 | 5.0 | 5.0 | 5.0 |
| C12-15 alkyl benzoate | 5.0 | 5.0 | 5.0 | 5.0 | 5.0 | 5.0 | 5.0 | 5.0 |
| ceteraryl alcohol | 2.0 | 2.0 | 2.0 | 2.0 | 2.0 | 2.0 | 2.0 | 2.0 |
| stearyl alcohol | 2.0 | 2.0 | 2.0 | 2.0 | 2.0 | 2.0 | 2.0 | 2.0 |
| ethylhexyl methoxycinnamate | 10.0 | 10.0 | | | | | | |
| polysilicone-15 | | | 5.0 | 5.0 | | | | |
| octocrylene | | | | | 8.0 | 8.0 | | |
| butyl methoxydibenzoyl methane | | | | | | | 3.0 | 3.0 |
| titanium dioxide | | | | | | | | |
| Water phase | | | | | | | | |
| aqua | Ad 100 | Ad 100 | Ad 100 | Ad 100 | Ad 100 | Ad 100 | Ad 100 | Ad 100 |
| glycerin | 3.0 | 3.0 | 3.0 | 3.0 | 3.0 | 3.0 | 3.0 | 3.0 |
| xanthan gum | 0.2 | 0.2 | 0.2 | 0.2 | 0.2 | 0.2 | 0.2 | 0.2 |
| Preservative (phenoxyethanol) | 1.0 | 1.0 | 1.0 | 1.0 | 1.0 | 1.0 | 1.0 | 1.0 |
| HBC1 (45% aq. solution) | | 6.0 | | 6.0 | | 6.0 | | 6.0 |
| Transfer [%][1] | 1.52 | 0.66 | 1.27 | 0.84 | 1.87 | 0.74 | 1.26 | 0.66 |
| Reduction [%][2] | | 56.58 | | 33.86 | | 60.43 | | 47.62 |

Material transfer of cosmetic compositions and respective reductions.

| Ingredient (INCI) | Ref. 5 | Ref. 6 | Ref. 7 | Ref. 8 |
|---|---|---|---|---|
| Oil Phase | | | | |
| potassium cetyl phosphate | 2.0 | 2.0 | 2.0 | 2.0 |
| dibutyl adipate | 5.0 | 5.0 | 5.0 | 5.0 |
| C12-15 alkyl benzoate | 5.0 | 5.0 | 5.0 | 5.0 |
| ceteraryl alcohol | 2.0 | 2.0 | 2.0 | 2.0 |
| stearyl alcohol | 2.0 | 2.0 | 2.0 | 2.0 |
| ethylhexyl methoxycinnamate | | | | |
| polysilicone-15 | | | | |
| octocrylene | | | | |
| butyl methoxydibenzoyl methane | | | | |
| titanium dioxide | 5.0 | 5.0 | | |
| Water phase | | | | |
| aqua | Ad 100 | Ad 100 | Ad 100 | Ad 100 |
| glycerin | 3.0 | 3.0 | 3.0 | 3.0 |
| xanthan gum | 0.2 | 0.2 | 0.2 | 0.2 |

TABLE 1-continued

| | | | | |
|---|---|---|---|---|
| Preservative (phenoxyethanol) | 1.0 | 1.0 | 1.0 | 1.0 |
| HBC1(45% aq. solution) | | 6.0 | | 6.0 |
| Transfer [%]1 | 1.05 | 0.82 | 1.02 | 0.72 |
| Reduction [%]2 | | 21.90 | | 29.41 |

[1]Material transfer of cosmetic composition in respect of composition applied to sponge.
[2]Reduction of material transfer as compared to respective reference (e.g. for 1: 56.58% = 100% − 100*(0.66/1.52)).
[1]Material transfer of cosmetic composition in respect of composition applied to sponge.
[2]Reduction of material transfer as compared to respective reference.

The results of table 1 clearly show that samples with the specific hyperbranched copolymer have a significant higher reduction in material transfer than the respective reference examples ("Ref.") without said copolymer. Furthermore, the results of table 1 also clearly shows the influence of organic solid or liquid UV-filter. It shows that the reduction of material transfer is much more pronounced if a combination of solid or liquid UV-filter and the specific hyperbranched copolymer as compared if no UV filter is used (Ref.5 and Ref.6, vs. 1-4). Furthermore, it can be seen that an organic UV-filter (1, 2, 3, 4) shows a significant higher reduction in material transfer than an inorganic UV-filter (Ref.5, Ref.6).

It further can be observed that polysilicone based UV filters (2) have a less pronounced reduction of material transfer than non-polysilicone based organic UV filter (1,3, 4).

The positive results and effect of reduction of material transfer by the composition according to the invention of the above experiments can also be found when the above compositions are applied to finger tips and a touch screen of an Samsung S9 display is touched with such a finger and the amounts of markings on the screen is visually assessed.

The invention claimed is:

1. A cosmetic composition comprising:
   (a) a hyperbranched copolymer of the monomers:
      (i) dodecenyl succinic acid anhydride,
      (ii) diisopropanol amine, and
      (iii) bis-dimethylaminopropyl amine, wherein
      the hyperbranched copolymer has a molecular weight Mn of between 1200 and 4000 g/mol and includes terminal groups of the formula:

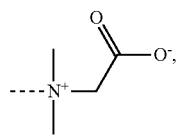

and
   (b) at least one liquid organic UV filter and/or at least one solid organic UV filter, wherein
   the cosmetic composition is a sun care composition.

2. The cosmetic composition according to claim 1, wherein the hyperbranched copolymer is prepared by consecutive steps of:
   a1) polymerizing the monomers (i), (ii) and (iii) to yield a polyesteramide having terminal dimethylamino groups of the formula

and thereafter
   a2) conducting quaternization of the dimethyl amino groups of the polyesteramide of step a1) by 2-chloroacetate.

3. The cosmetic composition according to claim 1, wherein the monomers (i) and (ii) are present in a molar ratio of the monomers (i) to the monomers (ii) of between 5:1 and 0.5:1.

4. The cosmetic composition according to claim 1, wherein the monomers (i) and (ii) are present in a molar ratio of the monomers (i) to the monomers (iii) of between 5:1 and 0.5:1.

5. The cosmetic composition according to claim 1, wherein the hyperbranched copolymer has a number average molecular weight Mn of between 1400 and 3000 g/mol.

6. The cosmetic composition according to claim 1, wherein the hyperbranched copolymer is polyquaternium-110.

7. The cosmetic composition according to claim 1, wherein the at least one solid organic UV filter comprises at least one solid organic UV(A) filter which is present in an amount of 0.1 to about 6 wt.-%, based on total weight of the cosmetic composition.

8. The cosmetic composition according to claim 1 wherein the at least one solid organic UV filter comprises at least one solid organic UV(B) filter which is present in an amount of 0.1 to about 6 wt.-%, based on total weight of the cosmetic composition.

9. The cosmetic composition according to claim 1, where the at least one liquid organic UV filter comprises at least one liquid organic UV(B) filter which is present in an amount of 0.1 to about 10 wt.-%, based on total weight of the cosmetic composition.

10. The cosmetic composition according to claim 1, wherein the composition comprises at least two UV filters of which at least one of the at least two UV filters is a solid or liquid organic UV(A) filter, and at least another of the at least two UV filters is a solid or liquid organic UV(B) filter.

11. The cosmetic composition according to claim 10, wherein the composition comprises a combination of:
   at least one solid organic UV(A) filter which is selected from the group consisting of bis-ethylhexyloxyphenol methoxyphenyl triazine, butyl methoxydibenzoyl methane, methylene bis-benzotriazolyl tetramethylbutylphenol and diethylamino hydroxybenzoyl hexyl benzoate; and
   at least one liquid organic UV(B) filter selected from the group consisting of ethylhexyl methoxycinnamate, octocrylene, homosalate, ethylhexyl salicylate, benzophenone-3 and drometrizole trisiloxane.

12. The cosmetic composition according to claim 1, wherein the composition is a sulfate-free cosmetic composition.

13. The cosmetic composition according to claim 1, wherein the composition is free of cationic emulsifier.

14. A method for reducing material transfer to a contacted surface of a cosmetic composition comprising at least one liquid organic UV filter and/or at least one solid organic UV filter, wherein the method comprises incorporating into the cosmetic composition an amount of a hyperbranched copolymer sufficient to reduce the material transfer of the cosmetic composition to the contacted surface, wherein the hyperbranched copolymer has a molecular weight Mn of between 1200 and 4000 g/mol and is a copolymer of the monomers:
(i) dodecenyl succinic acid anhydride,
(ii) diisopropanol amine, and
(iii) bis-dimethylaminopropyl amine, and wherein
the hyperbranched copolymer includes terminal groups of formula:

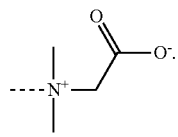

15. The method according to claim 14, wherein the contacted surface is a glass surface.

16. The method according to claim 14, wherein the contacted surface is a display of a mobile phone, computer device or tablet.

17. The method according to claim 14, wherein the hyperbranched copolymer is prepared by consecutive steps of:
a1) polymerizing the monomers (i), (ii) and (iii) to yield a polyesteramide having terminal dimethylamino groups of the formula

and thereafter
a2) conducting quaternization of the dimethyl amino groups of the polyesteramide of step a1) by 2-chloroacetate.

18. The method according to claim 14, wherein the monomers (i) and (ii) are present in a molar ratio of the monomers (i) to the monomers (ii) of between 5:1 and 0.5:1.

19. The method according to claim 14, wherein the monomers (i) and (ii) are present in a molar ratio of the monomers (i) to monomers (iii) of between 5:1 and 0.5:1.

* * * * *